United States Patent [19]

Keunecke et al.

[11] 4,285,871

[45] Aug. 25, 1981

[54] PROCESS FOR CONTINUOUSLY SEPARATING PHTHALIC ANHYDRIDE FROM THE REACTION GASES OF THE CATALYTIC OXIDATION OF O-XYLENE AND/OR NAPHTHALENE

[75] Inventors: Gerhard Keunecke, Geyen; Anton Klopfer, Cologne; Lothar Sterck, Hürth, all of Fed. Rep. of Germany

[73] Assignee: Davy International Aktiengesellschaft, Frankfurt, Fed. Rep. of Germany

[21] Appl. No.: 107,052

[22] Filed: Dec. 26, 1979

[30] Foreign Application Priority Data

Dec. 22, 1978 [DE] Fed. Rep. of Germany ....... 2855630

[51] Int. Cl.[3] .................... C07D 307/89

[52] U.S. Cl. .................... 260/346.7

[58] Field of Search .................... 260/346.7

[56] References Cited

U.S. PATENT DOCUMENTS

| | | | |
|---|---|---|---|
| 2,942,005 | 6/1960 | Brown et al. | 260/346.7 X |
| 4,071,540 | 1/1978 | Marquis | 260/346.7 X |

FOREIGN PATENT DOCUMENTS

| | | |
|---|---|---|
| 2323306 | 9/1973 | Fed. Rep. of Germany . |
| 832619 | 4/1960 | United Kingdom . |

*Primary Examiner*—Richard Raymond
*Attorney, Agent, or Firm*—Bernard & Brown

[57] ABSTRACT

Phthalic anhydride is continuously separated from the reaction gas mixture formed by the catalytic oxidation of o-xylene and/or naphthalene, by treating said reaction gas mixture with a maleic anhydride absorbent.

11 Claims, 1 Drawing Figure

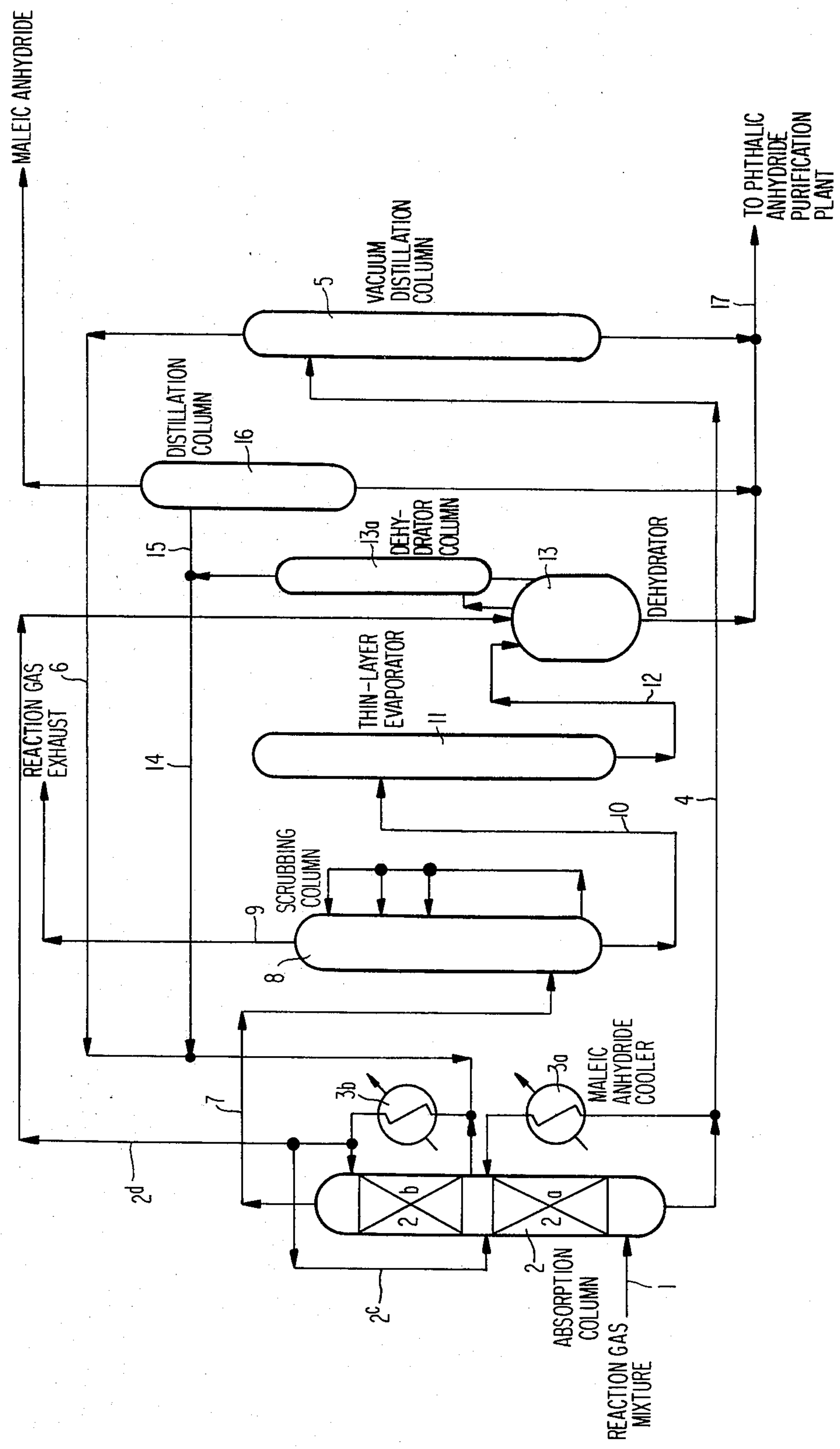
MALEIC ANHYDRIDE
TO PHTHALIC ANHYDRIDE PURIFICATION PLANT
VACUUM DISTILLATION COLUMN
5
17
DISTILLATION COLUMN
16
15
13a
DEHY-DRATOR COLUMN
13
DEHYDRATOR
REACTION GAS EXHAUST
6
THIN-LAYER EVAPORATOR
11
12
14
10
4
SCRUBBING COLUMN
9
8
7
3b
3a
MALEIC ANHYDRIDE COOLER
2d
2 b
2 a
2
2c
ABSORPTION COLUMN
1
REACTION GAS MIXTURE

PROCESS FOR CONTINUOUSLY SEPARATING PHTHALIC ANHYDRIDE FROM THE REACTION GASES OF THE CATALYTIC OXIDATION OF O-XYLENE AND/OR NAPHTHALENE

This invention relates to a process for the continuous separation of phthalic anhydride from the reaction gases resulting from the catalytic oxidation of o-xylene and/or naphthalene.

The catalytic oxidation of o-xylene or naphthalene with air produces a reaction gas with a relatively low content of phthalic anhydride. The large-scale separation, or sublimation, of phthalic anhydride is performed today in a stage-wise fashion, in melting condensers which are alternately cooled and heated, so as to separate out the phthalic anhydride content of the gas and to melt the phthalic anhydride off the cooled surfaces of the separator. Thus, at least two such apparatus units are necessary to remove the phthalic anhydride from the continuous stream of reaction gas.

The stage-wise method of operation of the separators is also disadvantageous with respect to the continuous purification of the raw phthalic anhydride. The loss of energy during the alternate heating and cooling is considerable, and the alternating thermal load leads to disturbances after a certain period of operation. This can result in a sealing loss, with the separated phthalic anhydride being polluted by the escaping heat-carrier oil, thereby lowering the product quality.

Washing out the phthalic anhydride from the reaction gas stream with a fluid scrubbing agent is also a conventional procedure. Thus, a mixture of phthalic anhydride and maleic anhydride can be washed out of the reaction gas stream with dibutyl phthalate or dipropyl phthalate. The maleic anhydride is distilled out of the scrubbing solution, the phthalic anhydride is crystallized out and separated, and the scrubbing agent is returned for further scrubbing contact with the gas stream after its impurities have been removed. This method is disadvantageous since the scrubbing agent must be successively subjected to distillation, crystallization, and purification before it can be returned for further scrubbing use. Furthermore, the resulting phthalic anhydride is polluted by the scrubbing agent (See U.S. Pat. No. 2,942,005).

In another procedure the reaction gas is scrubbed with tetradecane or pentadecane. To separate the phthalic anhydride, the loaded scrubbing solution is then subjected to azeotropic distillation. This procedure is not economical, since the azeotrope predominately consists of hydrocarbon, i.e. large quantities of hydrocarbon must be distilled in addition to the phthalic anhydride. Furthermore, the phthalic anhydride distillate thus produced still contains considerable quantities of hydrocarbon as an impurity (See British Patent Specification No. 832,619).

Finally, a procedure exists according to which the reaction gas is scrubbed with hydrocarbons primarily consisting of $C_{26-44}$ paraffins. In this procedure as well, it is necessary to crystallize out the phthalic anhydride for the scrubbing agent to be regenerated. In the process a 30–70% by weight mash is formed from which the remaining solution agent must be obtained through distillation. Here too a new impurity enters the phthalic anhydride from the scrubbing agent (See German OLS No. 2,313,306).

The objective of the present invention is to create a process for the continuous separation of phthalic anhydride from the reaction gas produced in the catalytic oxidation of o-xylene and/or naphthalene, a process in which no additional impurity enters the phthalic anhydride from the scrubbing agent and in which the scrubbing agent can be easily separated from the washed-out phthalic anhydride. In particular, the costs associated with the scrubbing agent are to be kept at a minimum. Further advantages of the inventive procedure will emerge from the following description.

In the process of treating the reaction gas mixture with an organic absorbent, removing the absorbent containing phthalic anhydride from the absorption zone, separating the absorbent from the phthalic anhydride, and returning the absorbent to the absorption zone, the objectives hereinbefore described are achieved, specifically, by treating the reaction gases with maleic anhydride, which can contain up to 85% by weight phthalic anhydride. A number of advantages are realized by scrubbing the reaction gases with maleic anhydride. Depending on the catalyst and the initial substance used for contact oxidation, the reaction gas will already contain maleic anhydride (e.g. 4–6% of the reaction product), so that no foreign substance enters the process with the new absorbent. The scrubbing agent, rather, is generally produced through the catalytic oxidation process itself, so that the inventive procedure is not dependent on any introduction of an absorbent from outside of the process. The product quality is not adversely affected, inasmuch as separation of the maleic anhydride from the phthalic anhydride presents no special problems. Since the scrubbing agent is produced in the process itself, and thus can be calculated among the prime costs, operating expenses for the procedure are small. This is true as well because the loaded absorbent need only be subjected to a two-part separation, whereas absorption of maleic anhyride and phthalic anhydride from a foreign substance, e.g. a hydrocarbon, requires three-part separation.

Even though pure maleic anhydride can be used as an absorbent, maleic anhydride containing phthalic anhydride is usually used so as to keep the costs of regenerating the absorbent within economical bounds. Thus, when maleic anhydride is mentioned below as the absorbent, this term also includes maleic anhydride mixtures containing up to 85% by weight phthalic anhydride. The absorbent does not, however, need to be a pure binary mixture of maleic anhydride and phthalic anhydride. Since the reaction gas can contain further impurities, e.g. benzoic acid, citraconic acid, o-toluic acid, etc., which can be absorbed by the absorbent in quantities dependent on conditions existing during absorption, the absorbent can contain varying quantities of these compounds, which remain in it, at least in part, during regeneration. Thus, the absorbent of the inventive procedure can contain in individual cases as much as 30% by weight or more of these impurities compounds.

As a rule, absorption can be performed in two or more stages, preferably in two stages. Packed columns are suitable as well as other apparatus for material exchange between gas and liquid in, for example, a counter-current arrangement. In the preferred arrangement of the inventive procedure, the temperature of the maleic anhydride in the absorption zone is kept between about 45° to 120° C. The absorbent enters the absorption zone at a low temperature and is heated there by the hot reaction gas and by the absorbed latent heat. To avoid too abrupt an increase in the temperature of the absorbent, which would impede the absorption effect, the absorbent is cooled. To achieve this, the absorbent is drawn out of the absorption stage(s) and after cooling in one or several external coolers, is returned to the absorption stages.

The reaction gas is preferably treated in the first absorption stage with a maleic anhydride/phthalic anhydride mixture containing 10 to 85% by weight phthalic anhydride at a temperature between approximately 90° to 120° C., and in the second or additional absorption stages with a maleic anhydride-containing absorbent comprising from 0 to about 30% by weight phthalic anhydride at a temperature between approximately 45° to 70° C. Each of the stages forming the absorption zone is equipped with its own absorbent cooling unit. In the first absorption stage the primary quantity of phthalic anhydride is washed out at a higher temperature with maleic anhydride having a higher concentration of phthalic anhydride. In the second absorption stage the smaller remaining content of phthalic is washed out of the gas at a lower temperature with regenerated maleic anhydride having a lower concentration of phthalic anhydride. In this fashion an extremely low level of phthalic anhydride in the final absorbent gas is achieved, and the amounts of maleic anhydride that are lost with the final gas due to the low vapor pressure in the second stage are slight.

In the preferred procedure, the reaction gas, with a temperature in the area of 135° to 200° C., preferably from 135° to 150° C., is introduced into the absorption zone, or, as the case may be, the first absorption stage, and withdrawn at a temperature from 45° to 80° C. from the absorption zone, or, as the case may be, the final absorption stage. As is the case with separation in the conventional melting separators, after leaving the reactor the reaction gas is initially cooled in a heat exchanger, e.g. a steam generator, to the temperature at which it first entered the absorption zone. The gas pressure within the absorption zone is generally between 1 and 1.2 atmospheres.

In a preferred arrangement the maleic anhydride, which is loaded with phthalic anhydride, is, after leaving the absorption zone, separated through distillation into a raw phthalic anhydride as a bottoms product and an overhead product primarily containing maleic anhydride; the overhead product is then returned into the absorption zone. The absorbent is regenerated through this simple distillative separation into two fractions. The overhead product returned to the absorption area should be 70 to 99% by weight maleic anhydride, preferably 80–90% by weight. The low boiling impurities which are absorbed by the absorbent from the process gas and which are lighter than phthalic anhydride partially accompany the maleic anhydride back into the absorption zone and are removed from the cycle with the corresponding concentration in the final absorbent gas. The remainder of the low boiling substances remains in the raw phthalic anhydride.

The raw phthalic anhydride produced as the bottoms product is given the usual preparatory treatment and then purified through distillation, e.g. in a continuous, two-stage distillation in which light, volatile impurities, such as residual maleic anhydride and benzoic acid, are distilled off in the first stage and the pure phthalic anhydride is distilled in the second as an overhead product. The distillative regeneration of the maleic anhydride containing phthalic anhydride is conducted at reduced pressure, e.g. from the range between 5 and 100 mm Hg. Naturally it is also possible to perform this separation at normal pressure.

In the preferred arrangement, the gas leaving the absorption zone and containing small amounts of maleic anhydride is scrubbed with water; the maleic acid solution recovered from this scrubbing is evaporated, the maleic acid is dehydrated and distilled, and a part of the maleic anhydride distillate is returned into the absorption zone. The remaining part is drawn off. In this manner the losses in maleic anhydride during the process are kept extremely low. The exhaust gas contains no more than 150 mg/$Nm^3$ maleic anhydride, phthalic anhydride, benzoic acid, and citraconic acid, and thus can be released into the atmosphere.

The maleic anhydride produced through oxidation less the losses occurring in the inventive procedure is available as a surplus product and increases the economy of the procedure. The inventive procedure is not, however, bound to this method of treating the exhaust gas; other purification procedures can be applied, in which the maleic anhydride formed through oxidation will generally cover the losses in maleic anhydride occurring in the course of the procedure. In the case of two or more stage absorption, a part of the mixture essentially consisting of maleic anhydride and phthalic anhydride, which has been drawn off from the second or additional absorption stage, is most effectively dehydrated and distilled, and the overhead product of distillation is returned into the second or additional absorption stage. The remaining part of the mixture is introduced into the first absorption stage.

The invention is more particularly described hereinafter with reference to the drawing in which the plant for implementation of the inventive procedure is schematically depicted.

The reaction gas to be purified enters through line 1 at the bottom of an absorption column 2, which is divided into two absorption stages $2^a$ and $2^b$. The maleic anhydride/phthalic anhydride mixture is circulated through both stages $2^a$, $2^b$ as an absorbent which can be cooled in the external coolers $3^a$ and $3^b$. A portion of the maleic anhydride containing phthalic anhydride at the bottom of the absorption column 2 reaches the vacuum-distillation column 5 through line 4; in the vacuum-distillation column 5 the mixture is separated into a raw phthalic anhydride as a bottoms product and a maleic anhydride with a low phthalic anhydride content as an overhead product. The raw regenerated absorbent reaches the second absorption stage $2^b$ of the absorption column 2 through line 6. A portion of the mixture drawn off from the second absorption stage $2^b$ is added to the first absorption stage $2^a$.

The gas from the absorption column 2 reaches the scrubbing column 8 through line 7; the gas is scrubbed at several levels with water or a maleic acid solution in the scrubbing column 8. The gas treated in this fashion is released through line 9 into the atmosphere. The temperature of this scrubbing stage is between 30° and 50° C. The maleic acid conducted into the cycle and enriched there to about 40% by weight passes from the scrubbing column 8 through line 10 into the thin-layer evaporator 11, in which the solution is concentrated to about 100% by weight maleic acid. The maleic acid passes from the thin-layer evaporator 11 through line 12 into the dehydrator 13 with a column $13^a$ above it, in which the acid is dehydrated into maleic anhydride.

The remaining portion of the absorption mixture drawn off from the second absorption stage $2^b$, which can be partially hydrated in stage $2^b$ due to the low temperature, is passed into the dehydrator 13 through line $2^d$. The maleic anhydride passing over the head in the dehydrator column in part returns through line 14 to the second stage $2^b$ of the absorption column 2, in part passes through line 15 into a distillation column 16, in which the pure maleic anhydride is distilled over the head. The residues from the dehydrator 13 and the column 16, which essentially consist of phthalic anhydride, benzoic acid, and citraconic acid, are purified with the raw phthalic anhydride from column 5 and are passed through line 17 to the phthalic anhydride purification plant (not shown).

EXAMPLE

An absorption and distillation pilot plant is used which comprises two absorption columns in series and a distillation column. The distillation column is provided for separating the absorbent from the raw product. The three columns are designed as packed columns with Raschig rings as the packing material.

A mixture comprising phthalic anhydride and maleic anhydride is used as the absorbent. About 8 $m^3$/h (0° C.; 1.013 bar) of a reaction gas obtained by catalytic oxidation of o-xylene with air are fed to the first absorption column at a temperature of about 150° C. The reaction gas contains about 500 g phthalic anhydride, about 30 g maleic anhydride and about 7 g other organic substances. A maleic/phthalic anhydride mixture containing about 42 weight percent phthalic anhydride is used as the absorbent in the first absorption column. The solidification point of this mixture is about 77° C. The temperature of the absorbent entering the first absorption column is about 81° C. The temperature of the reaction gas drops to about 95° C. at the exit from the first column. Under these conditions the pressure drop of the gas amounts to about 13 mbar.

About 1.3 kg/h of the absorbent mixture from the first absorption column are conducted to the distillation column operated at a head pressure of 25 mbar (a) and a bottom temperature of 165° C., and are separated. The composition of the head product is as follows: 5.7 weight percent phthalic anhydride; 94 weight percent maleic anhydride; 0.3 weight percent other organic substances. The respective condensation temperature is 82° C. About 0.8 kg/h of the head product are recycled to the second absorption column.

The reaction gas entering the second absorption column contains 0.27 weight percent phthalic anhydride; 8.3 weight percent maleic anhydride and 0.03 weight percent other organic substances. A phthalic/maleic anhydride mixture containing about 5 weight percent phthalic anhydride is used as the absorbent in the second absorption column. The solidification point of this mixture is about 49° C. The absorbent is heated by about 5° C. during the absorption. The absorbent from the second absorption column is cooled to about 56° C. In order to maintain the phthalic anhydride concentration constant about 1,8 kg/h of the pump circulated absorbent are circulated into the first absorption column.

The effluent gas from the second absorption column is saturated with absorbent and has a temperature of about 61° C. Its phthalic anhydride concentration amounts to about 470 mg/kg with a total percentage of organic substances of 2.2 weight percent. The effluent gas is scrubbed with maleic acid solution, and the scrubbing solution is processed in a known manner to produce maleic anhydride and phthalic anhydride. 0.2 kg/h maleic anhydride are recycled into the second absorption column in order to replenish a part of the absorbent loss.

What is claimed is:

1. In the process for the continuous separation of phthalic anhydride from the reaction gas of the catalytic oxidation of o-xylene and/or naphthalene whereby said reaction gas is treated with an organic absorbent in an absorption zone, the absorbent, which is loaded with phthalic anhydride is withdrawn from the absorption zone, the absorbent is separated from said phthalic anhydride, and the separated absorbent is returned to the absorption zone, the improvement which comprises treating the reaction gas with a maleic anhydride-based absorbent containing from 0 to about 85% by weight phthalic anhydride.

2. A process according to claim 1 wherein the temperature of the maleic anhydride-based absorbent in the absorption zone is kept within the range of from about 45° to 120° C.

3. A process according to claim 1 wherein the reaction gas is treated in a first absorption stage with a maleic anhydride/phthalic anhydride mixture containing 10 to 85% by weight phthalic anhydride, at a temperature in the range of about 90° to 120° C. and in one or more additional absorption stages with a maleic anhydride/phthalic anhydride mixture containing up to about 30% by weight phthalic anhydride at a temperature in the range of about 45° to 70° C.

4. A process according to claim 1 wherein the reaction gas is introduced into the absorption zone at a temperature in the range of about 135° to 200° C. and is withdrawn from the absorption zone at a temperature in the range of about 45° to 80° C.

5. A process according to claim 3 wherein the reaction gas is introduced into the absorption zone at a temperature within the range of from about 135° to 150° C. and is withdrawn from the absorption zone at a temperature within the range of from about 45° to 80° C.

6. A process according to claim 3, 4 or 5 wherein the maleic anhydride loaded with phthalic anhydride from the absorption zone is separated by distillation into raw phthalic anhydride as a bottoms product and an overhead product predominately comprising maleic anhydride, and wherein said overhead product is returned to the absorption zone.

7. A process according to claim 6 wherein an overhead product comprising about 70 to 99% by weight maleic anhydride is returned to the absorption zone.

8. A process according to claim 6 wherein the distillation is performed at a pressure between 5 and 100 mm Hg.

9. A process according to claim 1, 3, 4 or 5 wherein the reaction gas leaving the absorption zone is scrubbed with water to remove residual maleic anhydride and to thereby form a maleic acid solution; and wherein said maleic acid solution is evaporated, dehydrated and distilled, with one portion of the resulting maleic anhydride distillate being returned to the absorption zone and the other portion of said distillate being drawn off as product.

10. A process according to claim 6 wherein the reaction gas leaving the absorption zone is scrubbed with water to remove residual maleic anhydride and to thereby form a maleic acid solution; and wherein said maleic acid solution is evaporated, dehydrated and distilled, with one portion of the resulting maleic anhydride distillate being returned to the absorption zone and the other portion of said distillate being drawn off as product.

11. A process according to claim 3 or 10 wherein a portion of the absorbed mixture of maleic anhydride and phthalic anhydride, which absorbed mixture has been drawn off from the last absorption stage, is dehydrated and distilled, and the distillation product thereof is returned to the second absorption stage, and wherein the remaining portion of said absorbent mixture is added to the first absorption stage.

* * * * *